United States Patent [19]

Wu et al.

[11] Patent Number: 6,030,634
[45] Date of Patent: Feb. 29, 2000

[54] POLYMER GEL COMPOSITION AND USES THEREFOR

[75] Inventors: Chi Wu, Yeung Long; Suhong Jiang, Shatin, both of The Hong Kong Special Administrative Region of the People's Republic of China

[73] Assignee: The Chinese University of Hong Kong, Shatin N.T., The Hong Kong Special Administrative Region of the People's Republic of China

[21] Appl. No.: 08/990,497

[22] Filed: Dec. 15, 1997

Related U.S. Application Data

[60] Provisional application No. 60/033,897, Dec. 20, 1996.

[51] Int. Cl.[7] ........................................... A61L 17/10
[52] U.S. Cl. ............................................. 424/423; 424/487
[58] Field of Search ...................................... 424/422, 423

[56] References Cited

U.S. PATENT DOCUMENTS

| | | | |
|---|---|---|---|
| Re. 33,997 | 7/1992 | Kuzma et al. | 523/106 |
| 4,912,032 | 3/1990 | Hoffman et al. | |
| 5,226,902 | 7/1993 | Bae et al. | 604/892.1 |
| 5,403,893 | 4/1995 | Tanaka et al. | 525/218 |
| 5,580,929 | 12/1996 | Tanaka et al. | 525/218 |

FOREIGN PATENT DOCUMENTS

| | | |
|---|---|---|
| 0595226 | 5/1994 | European Pat. Off. |
| 8134146 | 5/1996 | Japan . |

OTHER PUBLICATIONS

Matsuo, Eriko Sato et al. "Kinetics of discontinuous volume–phase transition of gels." J. Chem. Phys. 89 (3), Aug. 1, 1988, pp. 1695–1703.

Tanaka, Toyoichi et al. "Collapse of gels in an electric field." Science, vol. 218, Oct. 29, 1982, pp. 467–469.

Gutowska, Anna et al. "Thermosensitive interpenetrating polymer networks: synthesis, characterization, and macromolecular release." Macromolecules, vol. 27, 1994, pp. 4167–4175.

Yoshida, Ryo et al. "Comb–type grafted hydrogels with rapid de–swelling response to temperature changes." Nature, vol. 374, No. 6519, Mar. 16, 1995, pp. 240–242.

Yoshida, Ryo et al. "Modulating the phase transition temperature and thermosensitivity in N–isopropylacrylamide copolymer gels." Journal of Biomater. Sci. Polymer Edn., vol. 6, No. 6, 1994, pp. 585–598.

(List continued on next page.)

*Primary Examiner*—Peter F. Kulkosky
*Attorney, Agent, or Firm*—Townsend and Townsend and Crew LLP; Kenneth R. Allen

[57] ABSTRACT

The present invention general relates to thermally responsive polymer gel compositions that have enhanced temperature-dependent shrinking rates, increased strength, and improved pliability over previously known polymer compositions. In particular, the compositions are thermally responsive polymer gel compositions comprising a hydrophobic polymer matrix and an interpenetrating hydrophilic polymer network disposed therein, such that the resulting polymer gel composition has enhanced thermal responsiveness relative to the hydrophobic polymer matrix alone. This combination results in polymer gels having these improved properties. In a particular aspect, the hydrophobic polymer matrix is poly(n-isopropylacrylamide) ("PNIPAAM") and the interpenetrating polymer network is supplied by incorporation of an amount of protein, typically gelatin, within the PNIPAAM. The compositions of the invention find particular use in surgical applications for the repair of damaged tissues, e.g., blood vessels, neurons, and the like, and in temperature-dependent drug delivery systems.

28 Claims, 7 Drawing Sheets

OTHER PUBLICATIONS

Yu, Hua et al. "Thermo–sensitive swelling behavior in crosslinked N–isopropylacrylamide networks: cationic, anionic, and ampholytic hydrogels." Journal of Applied Polymer Science, vol. 49, 1993, pp. 1553–1563.

Osada, Yoshihito et al. "Intelligent gels." Scientific American, May 1993, pp. 42–47.

Hoffman, Allan S. "Applications of thermally reversible polymers and hydrogels in therapeutics and diagnostics." Journal of Controlled Release, vol. 6, 1987, pp. 297–305.

Shibayama, Mitsuhiro et al. "Volume phase transition and related phenomena of polymer gels." Advances in Polymer Science, vol. 109, pp. 1–62.

Press Release, "High Shrinking Rate Biocompatible Polymer," Hong Kong Institute of Biotechnology Ltd., Sep. 1997.

Osada, Yoshihito & S.B. Ross–Murphy, "Intelligent Gels," Scientific. American, May 1993, vol. 268 No.5, pp. 82–87.

Kim, Yong–Hee, et al., "pH/Temperature–Sensitive Polymers for Macromolecular Drug Loading and Release," Journal of Controlled Release 28 (1994) pp. 143–152.

Ilavsky, Michal & Bouchal, Karel, "Phase Transition in Swollen Gels. 10. Effect of the Positive Charge and Its Position in the Side Chain on the Collapse And Mechanical Behaviour of Poly(Acrylamide) Networks," Institute of Macromolecular, Chemistry, Czechoslovak Academy of Sciences. No. 29: pp. 435–447.

Matsuo, Eriko Sato and Tanaka, Toyoichi, "Kinetics of Discontinuous Volume–phase Transition of Gels," J. Chem. Phys. 89(3), pp. 1695–1703, Aug. 1, 1998.

Sekimoto, Ken, "Temperature Hysteresis and Morphology of Volume Phase Transition of Gels," Physical Review Letters 70(26), pp. 4154–4157, Jun. 28, 1993.

Mahoney, Melissa J. and Saltzman, W. Mark, "Controlled Release of Proteins to Tissue Transplants for the Treatment of Neurodegenerative Disorders," Journal of Pharmaceutical Sciences 85(12), pp. 1276–1281, Dec. 1996.

Brannon–Peppas, Lisa, "Recent Advances on the Use of Biodegradable Microparticles and Nanoparticles in Controlled Drug Delivery," International Journal of Pharmaceutics, 116 (1995) pp. 1–9.

Rao, K. Panduranga, "Recent Developments of Collagen––Based Materials for Medical Applications and Drug Delivery Systems,"J. Biomater. Sci. Polymer Edn. 7(7), pp. 623–645 (1995).

Park, Tae Gwan and Hoffman, Allan S., "Thermal Cycling Effects of the Bioreactor Performances of Immobilized β–Galactosidase in Temperature–Sensitive Hydrogel Beads," "Papers" Enzyme Microb. Technol. vol. 15, pp. 476–482, Jun. 1993.

Gutowska, Anna et al., "Heparin Release From Thermosensitive Hydrogels," Journal of Controlled Release, 22 (1992), pp. 95–104.

POLYMER GEL COMPOSITION AND USES THEREFOR

This application is a regular application claiming priority to U.S. Provisional Patent Application Ser. No. 60/033,897, entitled "Novel Polymer Gel Composition and Uses Therefor," filed Dec. 20, 1996, and having inventors Chi Wu and Suhong Jiang. The 60/033,897 application is assigned to the Chinese University of Hong Kong and is hereby incorporated herein by reference in its entirety for all purposes.

BACKGROUND OF THE INVENTION

Recently, polymer gels, especially those stimuli-responsive "intelligent" gels, have attracted much attention for their potential biological and medical applications, i.e., as special adsorbents, as actuators, and in drug delivery devices. Y. Osada & S. B. Ross-Murphy, *Sci. Amer.* 268(5):82 (1993); BIOLOGICAL AND SYNTHETIC POLYMER NETWORKS (O. Kramer ed., Elsevier, London 1988); M. Shibayama & T. Tanaka, *Adv. Polym. Sci.* 109:1 (1993); T. Tanaka, I. Nishio, S. Sun, & S. Ueno-Nishio, *Science* 218:467 (1982); A. S. Hoffman, *J. Controlled Release* 6:297 (1987). A gel is a three-dimensional cross-linked polymer network swollen by a large quantity of solvent, whose properties fall between those of a liquid and those of a solid. For this reason, polymer gels are sometimes classified as wetware in order to distinguish them from software and hardware.

Despite a variety of interesting physical and chemical properties, synthetic gels are still used mainly in only a few applications, such as in foods, as water adsorbents, and in soft contact lenses. Two main obstacles—namely, the gel shrinking/swelling speed and strength—have limited many of the potential applications of gels. Much effort has been applied in the last two decades to overcome these two obstacles. For example, it has been reported that the slow shrinking rate can be attributed to the formation of a hard skin layer at very initial stage of the gel shrinking, which prevents further diffusion and outflow of solvent molecules, such as water molecules, from inside the gel. A. Gutowska et al., *J. Controlled Release* 22:95 (1992); T. G. Park & A. S. Hoffman, *Enzy. Microb. Technol.* 15:476 (1993); K. Sekimoto, *Phys. Rev. Lett.* 70:4154 (1993); H. Yu & D. W. Grainger, *J. Appl. Polym. Sci.* 49:1553 (1993); R. Yoshida et al., *J. Biomat. Sci.-Polym. Ed.* 6:585 (1994); Y. H. Kim et al., *J. Controlled Release* 28:143 (1994). Using another hydrophobic polymer to modify thermal sensitive polymer gels via an interpenetrating polymer network ("IPN") structure has also been reported. A. Gutowska et al., *Macromolecules* 27:4167 (1994); R. Yoshida et al., *Nature* 374:240 (1995). This leads to a stronger gel, and in some cases, a moderately improved shrinking rate. Most of the applications of these IPNs are in drug delivery. Recently, Yoshida et al. reported that grafting a hydrogel can increase its shrinking rate. R. Yoshida et al., *Nature* 374:240 (1995). However, preparation of such a comb-type grafted hydrogel is not a simple task.

It would therefore be desirable to provide an easily producible polymer gel composition which has improved shrinking rate and strength characteristics. The present invention meets these and other needs.

SUMMARY OF THE INVENTION

The present invention generally relates to polymer compositions that have enhanced temperature-dependent shrinking rates, increased strength, and improved pliability over previously known polymer compositions. In particular, the present invention provides thermally responsive polymer gel compositions comprising a hydrophobic polymer matrix and an interpenetrating hydrophilic polymer network disposed within the hydrophobic polymer matrix, wherein the polymer gel composition has enhanced thermal responsiveness as compared to the hydrophobic polymer matrix alone. This combination results in polymer gel compositions having improved properties, including increase shrinking rates, increased gel breaking strength, and other advantageous properties, such as described above. The compositions of the invention find particular use in surgical applications for the repair and reinforcement of damaged tissues, such as, for example, blood vessels, neurons, nerves, and the like, especially in warm-blooded animals. In addition, the compositions of the invention are particularly useful in in vivo and ex vivo surgical applications for sealing leaking or ruptured blood vessels and for joining two blood vessel segments or two nerve segments, and the like, especially in warm-blooded animals. In a particular aspect, the hydrophobic polymer matrix comprises poly(n-isopropylacrylamide) (PNIPAAM) and the interpenetrating hydrophilic polymer network comprises an amount of protein, typically gelatin, disposed within the PNIPAAM.

In another aspect, the invention provides a composition of matter which comprises a polymer gel comprising a thermally sensitive polymer matrix and a hydrophilic polymer network interpenetrating the thermally sensitive polymer matrix. The polymer gel is capable of shrinking at a greater rate in response to a change in temperature as compared to the thermally sensitive polymer matrix alone.

The invention also provides a thermally responsive biocompatible polymer gel composition, comprising a hydrophobic polymer matrix and an interpenetrating hydrophilic polymer network disposed within said hydrophobic polymer matrix, wherein the polymer gel composition has a shrinking rate that is greater than a shrinking rate of the hydrophobic polymer matrix.

In still another aspect, the invention provides an interpenetrating polymer network gel composition comprising a thermosensitive polymer, and a hydrophilic polymer interpenetrating the thermosensitive polymer. The thermosensitive polymer and the hydrophilic polymer are arranged with respect to each other so that at least one type of interaction develops between the thermosensitive polymer and the hydrophilic polymer. Such interaction is sufficient to cause the composition to shrink at a greater rate than the thermosensitive polymer alone at a temperature above a shrinking temperature of the composition.

The invention also provides thermally responsive polymer gel compositions formed into sheets or tubes. Such sheets and tubes find useful in various applications of the invention, including in methods for sealing severed or ruptured blood vessels and as prosthetic blood vessels for medical and surgical applications.

In another aspect, the invention provides a thermally responsive polymer gel composition comprising PNIPAAM and gelatin, and further comprising a chemical incorporated into the gel composition, said chemical capable of being released from the composition in response to an increase in the temperature of the gel composition to a temperature above a shrinking temperature of the composition.

In yet another aspect of the invention, methods for sealing a blood vessel system in vivo are provided. Such methods comprise providing a tube comprising a thermally responsive biocompatible polymer gel composition of the present invention, the tube having a first end and a second end, and an internal lumen therebetween, and the tube being maintained at a temperature of no more than about 32° C., and providing a severed blood vessel comprising a first end and a second end, the vessel being within a warm-blooded animal having a minimal internal ambient temperature of from about 25° C. to about 40° C., and more preferably, at least about 35° C. The first severed end of the blood vessel is inserted into the first end of the tube, and the second severed end of the blood vessel is inserted into the second end of the tube. The tube is allowed the tube to achieve the ambient temperature and to shrink around the first and second ends of the blood vessel, thereby sealing the blood vessel. For such methods, a preferred thermally responsive biocompatiable polymer gel composition comprises PNIPAAM and gelatin in relative amounts described herein below.

In yet another aspect, the invention provides an in vivo method for repairing a blood vessel system in a warm-blooded animal. The method comprises the steps of providing a tube comprising a thermally responsive polymer gel composition of the present invention, said tube having a first end, a second end, and an internal lumen therebetween, said tube being maintained at a temperature lower than a shrinking temperature of the polymer gel composition; providing a blood vessel system comprising a first blood vessel segment having an internal lumen and an end and a second blood vessel segment having an internal lumen and an end, said first and second blood vessel segments contained within the animal, said animal having a minimal internal ambient temperature greater than the shrinking temperature of the polymer gel composition; inserting the end of the first blood vessel segment into the first end of the tube; inserting the end of the second blood vessel segment into the second end of the tube such that tube is positioned over the first and second ends of the blood vessel segments; and maintaining the tube in position until the temperature of the tube achieves the internal ambient temperature of the animal and shrinks onto the blood vessel segments, thereby providing contiguous blood flow through the two blood vessel segments. For such methods, a preferred thermally responsive polymer gel composition comprises PNIPAAM and gelatin in relative amounts as described below.

Also provided are methods for sealing a blood vessel system in vivo in a warm-blooded animal which comprise the steps of providing a tube comprising a thermally responsive polymer gel composition according to the present invention, the tube having a first end and a second end, and an internal lumen therebetween, said tube being maintained at a temperature lower than a shrinking temperature of the polymer gel composition; providing a blood vessel system comprising a first blood vessel segment having an internal lumen and an end and a second blood vessel segment having an internal lumen and an end, said system being within a warm-blooded animal having a minimal internal ambient temperature that is greater than the shrinking temperature of the polymer gel composition; inserting the end of the first blood vessel segment into the first end of the tube and all the way through the tube such that the end of the first blood vessel segment emerges from the second end of the tube; connecting the end of the first blood vessel segment with the end of the second blood vessel segment with at least one surgical stitch; positioning the tube over the ends of the first and second blood vessel segments; and maintaining the tube in position until the temperature of the tube achieves the internal ambient temperature of the animal and shrinks onto the blood vessel segments, thereby providing contiguous blood flow through the two blood vessel segments and sealing the blood vessel system. For such methods, a preferred thermally responsive biocompatible polymer gel composition comprises PNIPAAM and gelatin in relative amounts as described below.

In another aspect, the invention provides methods for joining a first nerve segment and a second nerve segment of a nerve system in vivo in a warm-blooded animal comprising the steps of providing a tube comprising a thermally responsive polymer gel composition of the present invention, the tube having a first end and a second end, and an internal lumen therebetween, and the tube being maintained at a temperature lower than a shrinking temperature of the polymer gel composition; providing a nerve system comprising a first nerve segment having an end and a second nerve segment having an end, said first and second nerve segments being within a warm-blooded animal having a minimal internal ambient temperature that is greater than the shrinking temperature of the polymer gel composition; inserting the end of the first nerve segment into the first end of the tube and through the tube such that the end of the first nerve segment emerges from the second end of the tube; connecting the end of the first nerve segment with the end of the second nerve segment with at least one surgical stitch; positioning the tube over the ends of the first and second nerve segments; and maintaining the tube in position until the temperature of the tube equilibrates with the internal ambient temperature of the animal and shrinks onto the nerve segments, thereby joining the first and second nerve segments. For such methods, a preferred thermally responsive biocompatible polymer gel composition comprises PNIPAAM and gelatin in relative amounts as described herein below.

Also included are methods for reinforcing a blood vessel segment or nerve segment in vivo in a warm-blooded animal having a minimal internal ambient temperature of at least about 33° C. Such methods comprise the steps of providing a sheet comprising a thermally responsive polymer gel composition of according to the present invention, said sheet being maintained at a temperature of no more than about 30° C.; contacting said blood vessel segment or said nerve segment with the sheer, said blood vessel segment or said nerve segment being contained within the animal; using an applicator to form the sheet into a tube around the blood vessel segment or nerve segment; and maintaining the tube in position until the temperature of the tube achieves the internal ambient temperature of the animal and contacts the blood vessel segment or nerve segment, thereby reinforcing the blood vessel segment or nerve segment. For such methods, a preferred thermally responsive biocompatible polymer gel composition comprises PNIPAAM and gelatin in amounts as described below.

In addition, the invention provides methods for repairing a blood vessel system. Such methods comprise the steps of providing a tube comprising a thermally responsive polymer gel composition according to the present invention as described, the tube having a first end, a second end, and an internal lumen therebetween, said tube being maintained at a temperature below the shrinking temperature of the polymer gel composition; providing a blood vessel system comprising a first blood vessel segment having an internal lumen and an end and a second blood vessel segment having an internal lumen and an end, said system being maintained at a temperature below the shrinking temperature of the polymer gel composition; inserting the end of the first blood vessel segment into the first end of the tube; inserting the end of the second blood vessel segment into the second end of the tube such that tube is positioned over the first and second ends of the blood vessel segments; and increasing the temperature of the tube to a temperature equal to or greater than the shrinking temperature of the polymer gel composition so as to cause the tube to shrink and to contact the blood vessel segments to provide contiguous blood flow through the two blood vessel segments, thereby repairing the blood vessel system. Such a method can also be employed to repair or seal other tissues, including neuronal tissues.

In another aspect, the invention provides temperature-dependent implantable medical devices comprising a thermally responsive polymer gel composition of the present invention as described herein. Such devices may be in the form of a sheet for use in joining separated tissues or repairing damaged tissues.

The invention also provides temperature-dependent drug delivery systems and devices comprising a thermally responsive polymer gel composition of the present invention, as described herein, into which a biologically or physiologically active compound is incorporated. In such systems and devices, the compound is released from the composition in response to an increase in temperature of the composition.

Also provided are methods for releasing a biologically or physiologically active compound into a surrounding environment which comprise the steps of providing an implantable medical device, said device comprising a thermally responsive polymer gel composition of the present invention, as described herein, and a therapeutically effective amount of the biologically or physiologically active compound, said device being maintained at a temperature less than a shrinking temperature of the composition, said compound being released from the composition when a temperature of the composition is increased to a temperature equal to or greater than the shrinking temperature of the composition; implanting said device in a body of a warm-blooded animal having a minimal internal ambient temperature greater than the shrinking temperature of the composition; and allowing the temperature of the device to achieve the minimal internal ambient temperature of the animal such that the composition shrinks and the compound is released from the composition.

In yet another aspect, the invention provides methods for site-specific or systemic drug delivery into a warm-blooded animal in need thereof. Such methods comprise implanting an implantable medical device comprising the thermally responsive polymer gel composition of the present invention, as described herein, and a therapeutically effective amount of the biologically or physiologically active compound into an animal having a minimal internal ambient temperature that is greater than the shrinking temperature of the composition, such that the device shrinks when its temperature achieves the internal ambient temperature of the animal, thereby releasing and delivering the compound into the animal.

The invention also includes methods of releasing a chemical into an environment. Such methods comprise providing a thermally responsive polymer gel composition of the present invention, wherein said composition further comprises a chemical, and increasing a temperature of the composition to a temperature greater than the shrinking temperature of the composition such that the chemical is released from the composition into the environment.

In yet another aspect, the invention provides thermally responsive actuators comprising a polymer gel layer comprising the thermally responsive biocompatible polymer gel composition of the present invention, as described herein, disposed over a flexible planar element, wherein said flexible planar element is not substantially thermally responsive.

In still another aspect of the invention, methods of producing a thermally responsive polymer gel composition comprising at least one hydrophobic polymer matrix and at least one interpenetrating hydrophilic polymer network disposed within the hydrophilic polymer network are provided. Such methods comprise the steps of: (a) combining the hydrophobic polymer matrix and the interpenetrating hydrophilic polymer network; (b) agitating the product obtained from step (a) to form a mixture; and (c) placing the product step (b) into a vessel adapted to store or deliver the composition.

These and other embodiments of the present invention, as well as its advantages and features, are described in more detail in conjunction with the text below and attached figures.

DETAILED DESCRIPTION OF THE INVENTION

I. Definitions

Figure 1:
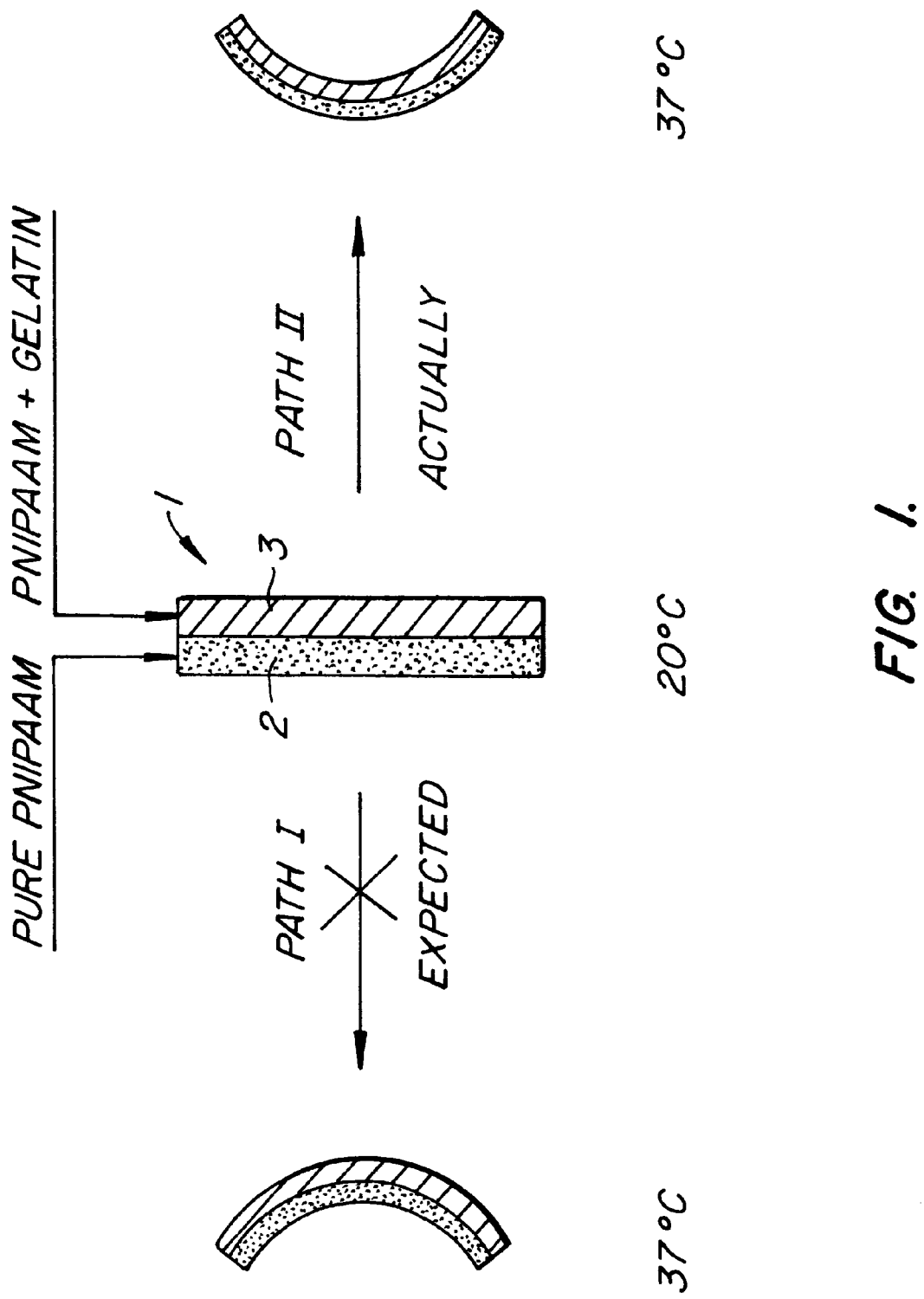
FIG. 1 is a schematic illustration of the effects of temperature on a double-layer gel strip comprising a layer of poly(n-isopropylacrylamide) (PNIPAAM) gel and a layer of PNIPAAM gel having gelatin disposed therein constructed in accordance with the principles of the present invention at temperatures 20° C. and 37° C., respectively.

Unless defined otherwise, all technical and scientific terms used herein have the same meaning as commonly understood by those of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). As used herein, the following terms have the meanings ascribed to them unless specified otherwise. Although any methods and materials similar or equivalent to those described herein may be used in the practice or testing of the present invention, the preferred methods and materials are described. For purposes of the present invention, the following terms are defined below.

The term "biocompatibility" or "biocompatible" as used herein refers to the manner and degree in which a material, such as a gel composition of the present invention, interacts with body tissues or fluids of an animal. A completely biocompatible material shows no effect or interaction with the body, a satisfactory biocompatible material shows only slight effect or interaction with the body, and an incompatible material elicits a severe reaction from the body that it contacts. See, e.g., KIRK-OTHMER, ENCYCLOPEDIA OF CHEMICAL TECHNOLOGY, Vol. 19 (3d ed. 1982).

The term "enhanced thermal responsiveness" as used herein means having an increased response to a change in temperature or an increased reaction due to a change in temperature. The term "thermally responsive" as used herein means affected by or responding to a change in temperature.

The term "thermosensitive" as used herein means sensitive to a change in temperature.

The term "subject" as used herein includes animals and humans.

The term "animal" as used herein includes mammals and humans.

II. Compositions of the Invention and Uses Thereof

The present invention is directed to novel polymer gel compositions and uses for these compositions. In particular, the present invention provides non-toxic polymer gel compositions comprising a hydrophobic polymer matrix and an interpenetrating hydrophilic polymer network disposed within the hydrophobic polymer matrix that results in improved properties, including gel breaking strength, pliability, and a faster shrinking rate. The introduction of the interpenetrating polymer network in the hydrophobic polymer matrix provides additional function groups which can be further utilized to bind the compounds, such as drugs and catalysts. The gel compositions of the present invention have applications in a variety of fields, including use as a prosthetic device for, e.g., repairing, joining, and/or sealing ruptured or severed blood vessels, neurons, nerves, or other tissues in vivo or ex vivo, or for reinforcing or augmenting structurally deficient blood vessels, neurons, nerves, or other tissues in vivo or ex vivo. These gel compositions also have a variety of other uses that will become apparent from the following disclosure, including uses as thermal actuators, thermally responsive membranes, resistance thermometers, and drug delivery devices. Such compositions of the invention are useful in methods for site-specific delivery of drugs, or systemic delivery of drugs, into warm-blooded animals in need thereof. In addition, such compositions are useful in applications requiring the release of a specific chemical into an environment, including a particular tissue environment of a warm-blooded animal.

By way of background, a number of water-soluble polymer systems (including those systems and compositions of the present invention) show critical behavior leading to a phase separation at elevated temperatures. The temperature at which a polymer gel system undergoes a phase separation is defined as the "lower critical solution temperature." See, e.g., A. S. Hoffman, *J. Controlled Release* 6:297 (1987); H. Yu & D. W. Grainger, *J. Appl. Polym. Sci.* 49:1553 (1993). Phase separation is typically observed as a large, discontinuous volume change.

When a polymer gel nears its critical solution temperature, the gel undergoes a volume change and associated phase transition from a low temperature, highly swollen gel network to a high temperature, collapsed or shrunken gel network. The phase transition can be caused by, for example, hydrophobic interaction, van der Waals forces, hydrogen bonding, or ionic interaction within the polymer gel. As the polymer gel shrinks, low-molecular compounds (e.g., a solvent, such as water) included in the polymer gel are discharged from the gel. At that time, precipitation may occur, which results in an increase in the density of the polymer gel.

The term "phase transition" as used herein in reference to a gel composition of the present invention refers to a change in volume of the gel composition between an expanded phase and a contracted (i.e., collapsed or shrunken) phase or vice versa. The phase transition has been identified with the increase in entropy of the solvent (i.e., water) in the polymer network with increasing temperature. As the gel dehydrates and collapses, it becomes relatively more hydrophobic. It is believed that the relatively hydrophobic polymer network undergoes a decrease in entropy with increasing temperature as the network collapses near the lower critical solution temperature. The overall contribution to the free energy of the gel system is negative, which leads to the spontaneous and reversible behavior at this critical temperature. H. Yu & D. W. Grainger, *J. Appl. Polym. Sci.* 49:1553 (1993). Typically, when a polymer gel is heated to a temperature equal to or above its lower critical solution temperature, the gel thus undergoes the phase transition, precipitating suddenly and reversibly over a narrow temperature range.

The thermal shrinking or swelling property of the polymer gel is a phase transition property which depends on a variety of conditions, including the structure of the polymer gel, the structure of the polymer molecules constituting the gel, the pH of the solution, the concentration of salt in the solution surrounding the gel, and the like conditions. When these conditions are fixed, the phase transition of the polymer gel occurs critically and reversibly over at a particular temperature (or over a narrow temperature range) corresponding to the set of fixed conditions. The temperature at which a polymer gel reversibly swells and shrinks under such a set of fixed conditions is defined as the phase transition temperature.

The phase transition of a polymer gel of the present invention can be set within a range of, for example, 5° C. and 95° C. by selecting the above-described conditions. The reversible phase transition is usually quite rapid (e.g., 1 second or less) if the heat transfer is conducted sufficiently quickly. Below or at the phase transition temperature, the polymer gel interacts significantly with the solvent surrounding the gel (e.g., water) and absorbs a large amount of the solvent into the gel network. Thus, when the gel is below or at its phase transition temperature, the gel is in a swelled state. When the temperature of the polymer gel is equal to or greater than the phase transition temperature, the polymer gel typically undergoes a phase transition, thereby increasing the interactions between the chains of the polymer and causing the polymer gel to shrink and discharge solvent from the gel network. As the gel shrinks, its structure changes from a relatively hydrophilic form to a relatively hydrophobic form.

The temperature at which a polymer gel composition according to the present invention shrinks is termed the "shrinking temperature." The shrinking temperature depends on a variety of conditions, including the particular composition of the polymer gel, including the relative amounts of the hydrophobic polymer matrix and hydrophilic polymer network which interpenetrates the hydrophobic polymer matrix. A polymer gel composition of the present invention may shrink over a narrow temperature range.

In one aspect, the invention provides thermally responsive polymer gel compositions comprising a hydrophobic polymer matrix and an interpenetrating hydrophilic polymer network disposed within or interpenetrating the hydrophobic polymer matrix. The polymer gel composition has enhanced thermal responsiveness as compared to the hydrophobic polymer matrix alone. In such compositions, the enhanced thermal responsiveness generally comprises and is manifested by a shrinking rate that is greater than the shrinking rate of the hydrophobic polymer matrix alone at a temperature equal to or greater than the shrinking temperature of the composition. The shrinking rate is the rate at which the gel composition shrinks in response to a change in condition (e.g., increase in temperature). That is, the shrinking rate is determined by the time required for a gel to shrink from its fully swollen state to its fully collapsed state.

The shrinking rate of the polymer gel composition may be increased or decreased by varying a ratio of an amount of hydrophobic polymer matrix to an amount of interpenetrating hydrophilic polymer network in said polymer gel composition.

Such polymer gel compositions may further comprise an amount of a hydrophobic monomer or an amount of a hydrophilic monomer sufficient to cause a shrinking temperature of said polymer gel composition to increase or decrease. In such compositions, the hydrophobic monomer or hydrophilic monomer copolymerizes with the hydrophobic polymer matrix of said composition.

In a particular aspect, the polymer gel compositions of the present invention comprise a temperature-sensitive hydrophobic matrix, such as PNIPAAM gel, that is modified with an interpenetrating polymer network ("IPN") which leads to a faster shrinking and stronger gel composition. Examples of such IPNs include, e.g., protein, such as gelatin and collagen. Gelatin and collagen are among the preferred proteins for forming IPNs in polymer gel compositions of the present invention. In a preferred aspect, such compositions include gelatin in an amount of from about 0.1% to about 25% by weight based on the total weight of the gel composition, which includes PNIPAAM, gelatin, and water. Preferably, the composition comprises gelatin in an amount of from about 0.5% to about 5% by weight, or even more preferably, in an amount of from about 1% to about 3% by weight, based on the total weight of the gel composition (i.e., w/w) . In another preferred aspect, compositions according to the present invention comprise PNIPAAM in an amount of from about 5% to about 30% by weight based on the total weight of the composition. In polymer gel compositions of the present invention comprising PNIPAAM and gelatin, the shrinking temperature of the composition is typically about 35° C.

Such polymer gels comprising PNIPAAM modified with an IPN of gelatin have the surprising properties of having increased shrinking rates and enhanced strength over other polymer gel compositions. PNIPAAM is a water-soluble, relatively hydrophobic polymer network that undergoes phase transition at a temperature equal to or greater than its lower critical solution temperature. The lower critical solution temperature of a PNIPAAM gel is typically between about 31° C. and about 33° C. At temperatures below its lower critical solution temperature, the PNIPAAM gel is soluble in aqueous media. R. Yoshida et al., *Nature* 374:240 (1995). Above its lower critical solution temperature, the PNIPAAM gel undergoes a discontinuous phase transition, precipitating from solution suddenly and reversibly over a narrow temperature range. See R. Yoshida et al., *Nature* 374:240 (1995); E. S. Matsuo et al., *J. Chem. Phys.* 89(3) :1695 (1988).

PNIPAAM gels usually undergo a phase transition from a low-temperature, highly water-swollen polymer gel network to a high-temperature, collapsed dehydrated polymer network at a temperature at or above the lower critical solution temperature. The phase transition of the PNIPAAM polymer network typically causes a large discontinuous volume change. E. S. Matsuo et al., *J. Chem. Phys.* 89(3):1695 (1988); K. Sekimoto, *Phys. Rev. Lett.* 70:4154 (1993). In particular, PNIPAAM gels are known to shrink as much as about 10 to about 100 times in volume when heated above about 32° C.

Conversely, chemically cross-linked gelatin gels are known to swell slightly under similar conditions. Accordingly, one would expect that a gel comprising a combination of PNIPAAM gel and gelatin would have a shrinking rate reflective of the two polymers, e.g., a slower shrinking rate than PNIPAAM. Surprisingly, it has been discovered that contrary to expectations, a gel composition comprising PNIPAAM modified with an IPN of gelatin has a shrinking rate that is greater than that of pure PNIPAAM gel, in addition to other advantageous properties.

This discovery is reflected in FIG. 1, which shows a schematic illustration of a shrink-rate experiment using a strip (1) comprising a layer (2) of pure PNIPAAM gel and a layer (3) of a PNIPAAM gel incorporating 1% (w/w) gelatin by weight based on the total weight of the gel composition. The strip was prepared by adding gelatin to pre-polymerized PNIPAAM composition and initially maintained at a temperature of less than about 35° C. The cross-linking densities of the PNIPAAM gel networks were identical at both sides. It was anticipated that upon heating to a temperature greater than 35° C., the strip (1) would bend in the direction of the pure PNIPAAM gel layer (2) (i.e., following Path I), because it was expected that the pure PNIPAAM gel layer (2) would shrink more quickly and to a greater degree than the PNIPAAM+gelatin gel layer (3). However, upon heating, the strip was observed to bend in the direction of the PNIPAAM+gelatin gel layer (3), following Path II. This result indicated that the hybridized PNIPAAM+ gelatin gel layer (3) shrank more quickly than pure PNIPAAM gel layer (2) and thus that the PNIPAAM+gelatin combination had a shrinking rate (i.e., deswelling rate) greater than that of the pure PNIPAAM gel.

It is known that at about 32° C. the interactions between the chains of pure PNIPAAM intensify, thereby increasing the relative hydrophobicity of the PNIPAAM. In contrast, the gelatin remains hydrophilic in nature at this temperature. As the relative hydrophobicity of the PNIPAAM increases, the PNIPAAM and gelatin become more incompatible, resulting in a microscopic phase separation between the PNIPAAM and gelatin networks. This microscopic phase separation is believed to prevent the formation of a dense, hard skin layer on the surface of the PNIPAAM+gelatin gel composition and to result in the production of a number of hydrophilic channels (particularly in the gelatin network) through which solvent molecules (e.g., water molecules) can diffuse out of the gel composition. Thus, with the incorporation of gelatin in the PNIPAAM polymer matrix, water molecules are able diffuse out of the gel more freely and the resulting PNIPAAM+gelatin gel composition shrinks much faster as the temperature of the resulting is increased above it shrinking temperature (which corresponds generally to its phase transition temperature or lower critical solution temperature).

Figure 2:
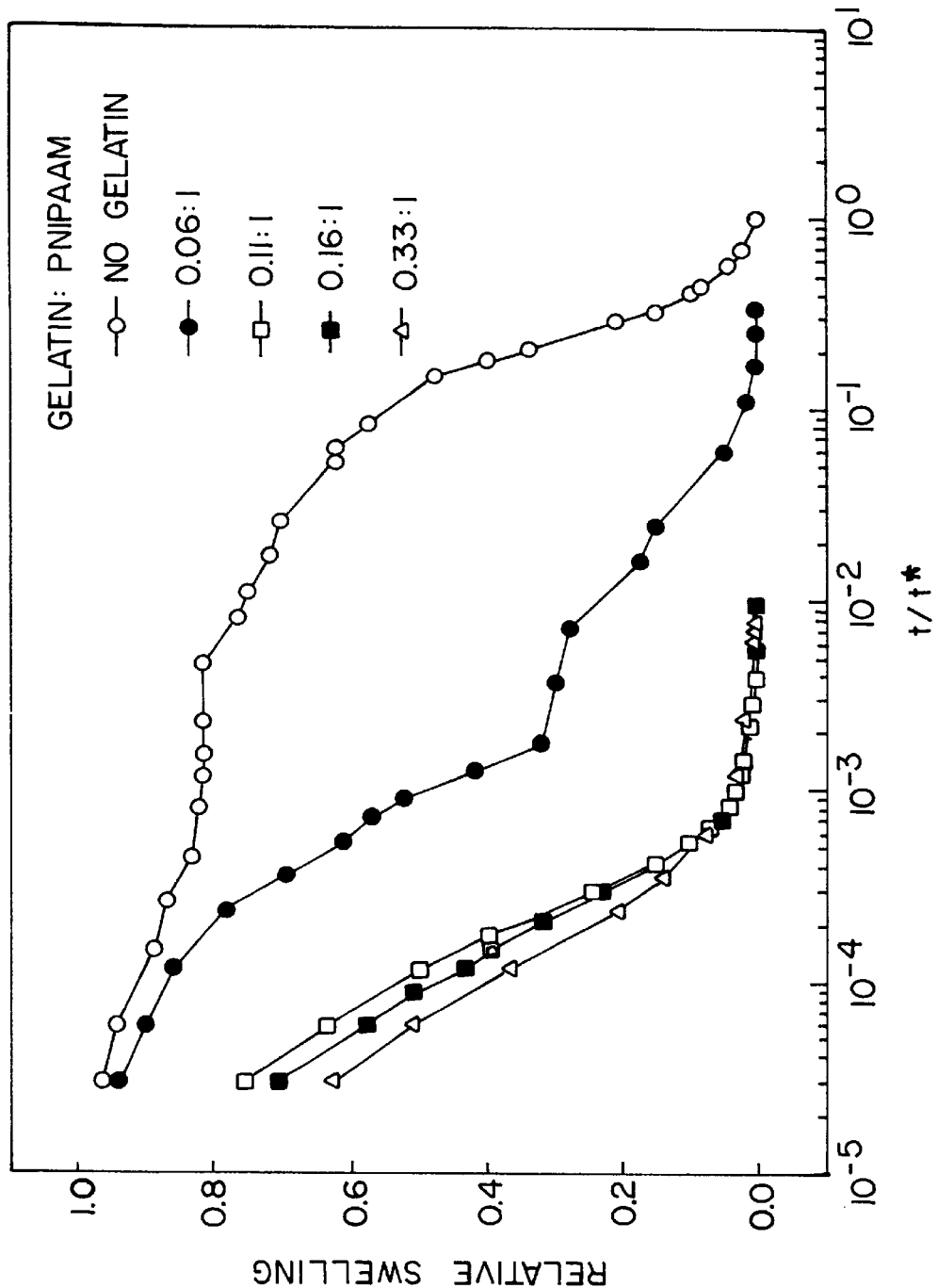
FIG. 2 is a graphic illustration of the relative swelling of thermally responsive polymer gel compositions of the present invention at a temperature of 37° C.

A quantitative study shows that incorporating gelatin into the PNIPAAM gel in an amount of about 1% by weight based on the total weight of the resulting gel composition can shorten the shrinking time of the PNIPAAM gel at about 37° C. by approximately three orders of magnitude. For example, FIG. 2 shows a comparison of shrinking kinetics as a function of time at 37° C. for PNIPAAM gel compositions in which various amounts of gelatin have been incorporated. In this study, gel compositions comprising various ratios of gelatin: PNIPAAM, including 0.06:1 (solid circles), 0.11:1 (open squares), 0.16:1 (solid squares), and 0.33:1 (open triangles) were compared with pure PNIPAAM gel compositions (open circles) (FIG. 2). The term "relative swelling" is defined as $(\Delta W)_t/(\Delta W)_o$, where $(\Delta W)t$ and $(\Delta W)_o$ represent the weight difference between the swollen gel and the fully collapsed gel at time t and at time t=0 (i.e., the fully swollen state), respectively. The term "t/t*" is defined as the reduced time, where t is the time at which a measurement is taken and t* is the time required for a pure PNIPAAM gel to reach its fully collapsed or shrunken state.

In this study, the gel composition was formed into the shape of a disk having a diameter of about 15 mm and a thickness of about 2 mm and was stored in deionized water at 20° C. prior to performing the experiment. The shrinking process was conducted in deionized water having a temperature of about 37° C. During the shrinking process, the gel was removed from the deionized water at specific time intervals (t), weighed and then put back into the deionized water. As is clear from the data presented in FIG. 2, the shrinking rate (also known as the "deswelling rate") of the gel composition increased as an increasing amount of gelatin was added to the composition. For several PNIPAAM/gel compositions shown in FIG. 2, the shrinking rate increased by approximately three orders of magnitude.

Figure 3:
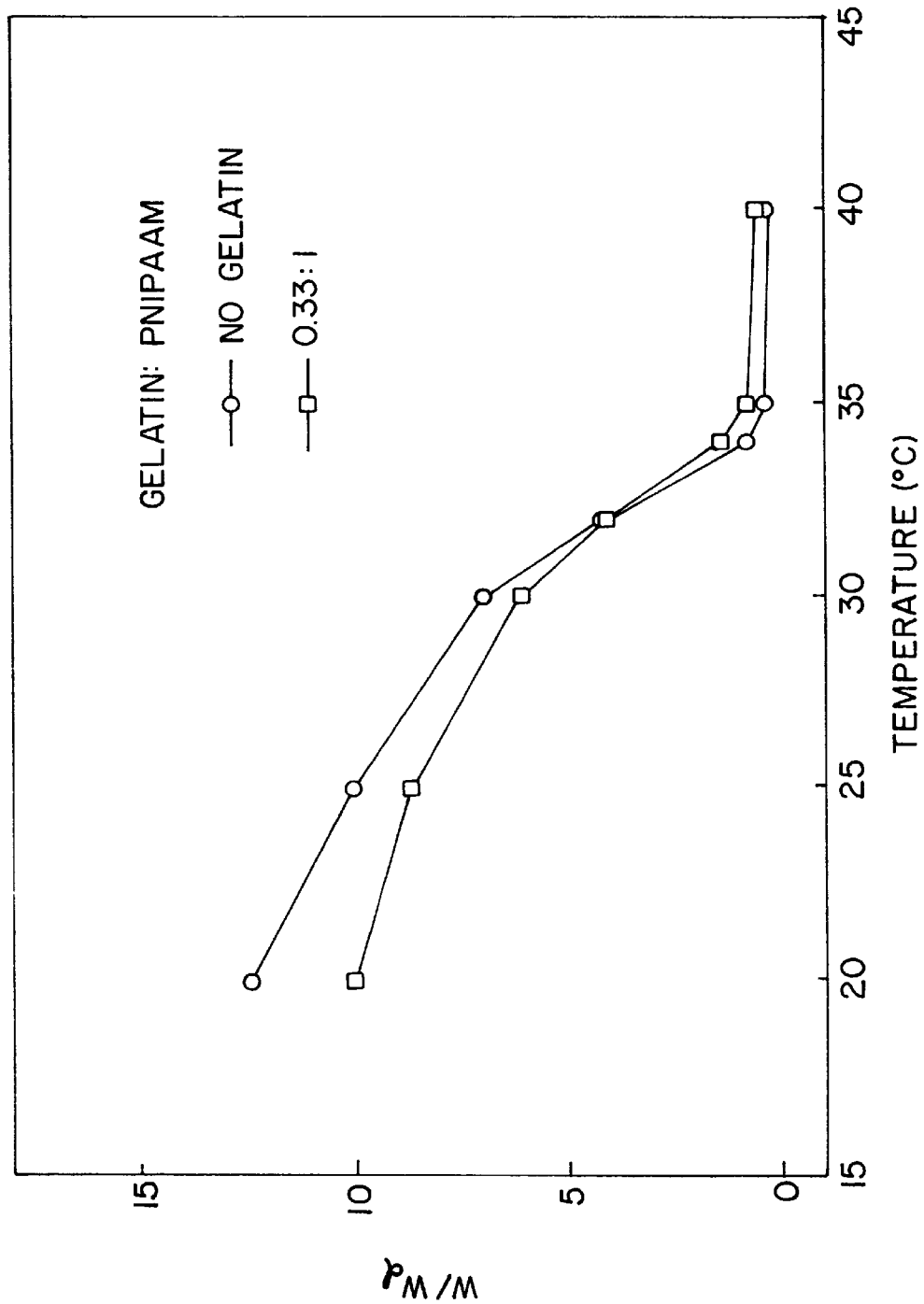
FIG. 3 is a graphical illustration of the shrinking ratios ($W_t/W_d$), as a function of temperature, of pure PNIPAAM gel and a polymer gel composition of the present invention comprising PNIPAAM and gelatin in a ratio of 0.33 gelatin to 1 PNIPAAM.

Notably, despite the enhanced shrinking rate, the amount of shrinkage between PNIPAAM and PNIPAAM/gelatin compositions was relatively similar. This is illustrated in FIG. 3, which shows a comparison of the "shrinking ratio" $(W/W_d)$, as a function of temperature, for a pure PNIPAAM gel and a gel composition comprising a ratio of gelatin to PNIPAAM of 0.33 to 1. The shrinking ratio is defined as $W/W_d$, where W is the weight of water inside the gel and $W_d$ is the weight of the dry gel (i.e., fully collapsed gel).

In this study, the shrink ratio was only altered by a factor of about 20% (see FIG. 3). It should be noted that maintaining a proper shrinking ratio is crucial for many applications wherein the volume change is utilized.

In another example, incorporation of gelatin (about 1 to about 3% (w/w)) into a hydrophobic polymer matrix (e.g., PNIPAAM) was found to enhance or increase the gel breaking strength by three times at a temperature lower than a shrinking temperature of the polymer gel composition, thereby providing a further advantage of composition of the invention. The gel breaking strength refers to the relative amount of force or pressure needed to break, crack, or fracture the polymer gel composition. In particular, incorporation into PNIPAAM of at least about 1% gelatin by weight based on the total weight of the composition was found to increase the gel breaking strength of the composition in its fully swollen state as compared to PNIPAAM alone.

In another aspect, the invention provides a composition of matter which comprises a polymer gel comprising at least one thermally sensitive hydrophobic polymer matrix and at least one hydrophilic polymer network interpenetrating said at least one thermally sensitive hydrophobic polymer matrix. The polymer gel is capable of shrinking at a greater rate in response to a change in temperature as compared to the thermally sensitive polymer matrix alone. Such compositions are especially useful in repairing, reinforcing, and/or sealing blood vessel tissues and segments and nerve tissues as described herein, and for use in drug delivery devices, systems and methods, and methods for releasing chemicals into particular environments.

In yet another aspect, the invention provides thermally responsive polymer gel composition that is especially suitable for applications and uses in animals and humans, as described herein. Such a composition may comprise a thermally responsive biocompatible polymer gel composition. Such compositions comprise a hydrophobic polymer matrix and an interpenetrating hydrophilic polymer network disposed within the hydrophobic polymer matrix, wherein the resulting composition has a shrinking rate that is greater than the shrinking rate of the hydrophobic polymer matrix alone. In a preferred aspect, the hydrophobic polymer matrix comprises poly(n-isopropylacrylamide) (PNIPAAM) and the hydrophilic polymer network comprises a protein, such as collagen or gelatin.

In still another aspect, the invention provides an interpenetrating polymer network gel composition comprising a thermosensitive polymer and a hydrophilic polymer interpenetrating the thermosensitive polymer. The thermosensitive polymer and the hydrophilic polymer are arranged with respect to each other in the composition so that at least one type of interaction develops between the thermosensitive polymer and the hydrophilic polymer. Such interaction is sufficient to cause the composition to shrink at a greater rate than the thermosensitive polymer alone at a temperature above a shrinking temperature of the composition.

Protein is a representative example of a hydrophilic polymer that may be employed in compositions of the invention. Other hydrophilic polymers, such as poly (acrylamide) and poly(vinyl alcohol), can also be used to promote the shrinking rate. Gelatin is a type of protein that may be employed as an IPN in compositions of the invention. Gelatin may be selected from the group consisting of gelatin A and gelatin B. Gelatin A is gelatin extracted in an acidic medium and gelatin B is a gelatin extracted in a basic medium.

In addition to PNIPAAM gels, derivatized PNIPAAM gels can also be used in compositions of the invention, and such gels can have different shrinking temperatures. Polymer gels comprising derivatized PNIPAAM modified with hydrophilic protein IPN(s) exhibit increased shrinking rates and increased strength over other polymer gel compositions (as well as particular properties pertaining to the derivatized PNIPAAM gel itself). The PNIPAAM gel can be modified or derivatized by copolymerizing another type of hydrophilic or hydrophobic monomer into the PNIPAAM backbone chains (i.e., into the network) such that the shrinking temperature is shifted to a particularly desired range (e.g., a narrow range within a range of 5° C. and 95° C.). Suitable monomers that can be used for polymerization include acrylate (hydrophobic) and acrylic (hydrophilic) acids, such as, for example, acrylic acid, methacrylate, methacrylic acid, acrylamide, methacrylamide, vinyl acetate, styrene, and their derivatives.

In still another example of the present invention, polymer gel compositions according to the present invention (e.g., including thermally responsive polymer gel compositions, thermally responsive biocompatible polymer gel compositions, and interpenetrating polymer network gel compositions) can be prepared which can selectively capture or incorporate a chemical from a liquid medium that passes through the interpenetrating network of the gel composition. For example, such a chemical can be included in the solvent in which the gel is prepared and thus incorporated or captured by the gel network when the gel composition is in its fully swollen state in the solvent. The chemical is effectively trapped inside the interpenetrating polymer gel network. Such a chemical is capable of being released from the composition to the surrounding environment when in response to an increase in the temperature of gel composition to a temperature above the shrinking temperature (or phase transition temperature) of the composition. That is, as the gel network dehydrates and collapses during phase transition in response to the temperature change, the chemical is discharged and released from the network. Chemicals that may be incorporated or captured by the gel networks in heavy metal ions, such as copper ($Cu+^2$) and lead ($Pb+^2$) ions.

In yet another illustration of the invention, the shrinking temperature (and phase transition temperature) of a polymer gel composition of the present invention are typically dependent on the particular nature and components of the composition. In general, increasing the amount of comonomer in the gel by direct copolymerization increases the lower critical solution temperature of the system and broadens the temperature range of the phase transition. H. Yu & D. W. Grainger, *J. Appl. Polym. Sci.* 49:1553 (1993). For example, the shrinking temperature of a polymer gel composition of the invention can be adjusted, changed, or varied (in the range of from about 20° C. to about 50° C.) by copolymerizing or incorporating a small amount of a hydrophobic or hydrophilic monomer into a hydrophobic polymer matrix (e.g., PNIPAAM) which has a hydrophobic polymer network disposed therein.

Generally, a polymer gel composition of the invention comprising a hydrophobic polymer matrix and an interpenetrating polymer network disposed within the hydrophobic polymer matrix exhibits an enhanced thermal responsiveness as compared to the hydrophobic polymer matrix alone. The enhanced thermal responsiveness of the composition may comprise an increased shrinking rate at an elevated temperature as compared to the hydrophobic polymer matrix alone. In particular, the enhanced thermal responsiveness of the composition is observed in an increased shrinking rate at temperatures above about 35° C., and preferably above about 37° C. The temperature range of the shrinking temperature can be shifted to higher or lower values (e.g., from about 5° C. to about 95° C.) by a copolymerization of either hydrophilic or hydrophobic monomers into the PNIPAAM network.

The enhanced thermal responsiveness of the composition may also comprise an increased gel breaking strength at temperatures above about 35° C., and preferably above about 37° C., as compared to the hydrophobic polymer matrix alone.

In another aspect of the invention, the shrinking rate and the shrinking temperature of polymer gel compositions of the present invention can be increased or decreased (i.e., adjusted) by varying a ratio of an amount of hydrophobic polymer matrix to an amount of interpenetrating hydrophilic polymer network disposed within or interpenetrating the hydrophobic polymer matrix. In a preferred aspect, where the gel composition comprises PNIPAAM with an IPN of gelatin incorporated therein, the relative increase in the shrinking rate (alternatively, deswelling rate) of the composition, for example, is found to increase for ratios of PNIPAAM/gelation of 0.06/1, 0.11/1, 0.16/1, and 0.33/1, respectively.

The polymer gel compositions of the invention are capable of reversibly swelling and shrinking by changing the temperature of such compositions to a temperature below or above the lower critical solution temperature.

In another illustration of the invention, the polymer gel compositions of the invention may comprise at least a first polymer matrix and a second polymer network interpenetrating said first polymer matrix, wherein the gel is capable of undergoing a phase separation in response to a change in temperature so that the gel shrinks at a greater rate when temperature is increased and swells at a greater rate when temperature is decreased as compared to the first polymer matrix alone.

In another aspect, the invention provides gel compositions exhibiting a reversible temperature-dependent phase separation and a lower solution critical temperature. Such compositions comprise a hydrophobic polymer matrix, and a hydrophilic polymer network which is typically in an amount of from about 0.1% to about 25% by weight based on the total weight of the composition, wherein the composition has an increased shrinking rate at a temperature above the lower solution critical temperature as compared to the hydrophobic polymer matrix alone.

The present invention has many applications. For example, the gel compositions of the invention may be used in potential biological and medical applications, including as special adsorbents, as actuators, in drug delivery devices, and for site-specific or systemic drug delivery methods. In an especially preferred aspect, the compositions of the present invention may be used for surgical applications, including those used for surgical treatment of animals and humans in need thereof. In particular, the fast-shrinking and stronger polymer gels of the invention may be used to repair damaged blood vessels, e.g., connect severed vessels, reinforce weakened vessels, or patch ruptured vessels in vivo. Similarly, these compositions can be used to repair neurons or other tissues. In these uses, the polymer gel compositions will often be fabricated in a tubular format or in a planar sheet to facilitate their use in these applications. For example, the polymer gels may be formed into tubes or sheets which may be used to surround or encase ruptured or severed tissues or vessels, thereby assisting with connection and repair of such tissues or vessels.

The invention also provides in vivo or ex vivo methods for repairing a blood vessel system in a warm-blooded animal. Such methods comprises the steps of: (a) providing a tube comprising a thermally responsive polymer gel composition of the invention, said tube having a first end, a second end, and an internal lumen therebetween, said tube being maintained at a temperature lower than a shrinking temperature of the polymer gel composition; (b) providing a blood vessel system comprising a first blood vessel segment having an internal lumen and an end and a second blood vessel segment having an internal lumen and an end, said first and second blood vessel segments contained within the animal, said animal having a minimal internal ambient temperature greater than the shrinking temperature of the polymer gel composition; (c) inserting the end of the first blood vessel segment into the first end of the tube; (d) inserting the end of the second blood vessel segment into the second end of the tube such that tube is positioned over the first and second ends of the blood vessel segments; and (e) maintaining the tube in position until the temperature of the tube achieves the internal ambient temperature of the animal and shrinks onto the blood vessel segments, thereby providing contiguous blood flow through the two blood vessel segments.

In a preferred aspect of such method, the hydrophobic polymer matrix comprises PNIPAAM and the interpenetrating polymer network comprises gelatin. The shrinking temperature of the polymer gel composition employed in such methods is typically at least about 32° C., and the minimal internal ambient temperature of the animal is at least about 33° C.

Other methods for repairing a blood vessel system are also provided. Such methods, for example, comprise the steps of: (a) providing a tube comprising a thermally responsive polymer gel composition of the invention, the tube having a first end, a second end, and an internal lumen therebetween, said tube being maintained at a temperature below the shrinking temperature of the polymer gel composition; (b) providing a blood vessel system comprising a first blood vessel segment having an internal lumen and an end and a second blood vessel segment having an internal lumen and an end, said system being maintained at a temperature below the shrinking temperature of the polymer gel composition; (c) inserting the end of the first blood vessel segment into the first end of the tube; (d) inserting the end of the second blood vessel segment into the second end of the tube such that tube is positioned over the first and second ends of the blood vessel segments; and (e) increasing the temperature of the tube to a temperature equal to or greater than the shrinking temperature of the polymer gel composition so as to cause the tube to shrink and to contact the blood vessel segments to provide contiguous blood flow through the two blood vessel segments, thereby repairing the blood vessel system.

In addition, in another aspect, the invention provides methods for sealing a blood vessel system in vivo in a warm-blooded animals. Such methods comprise the steps of: (a) providing a tube comprising a thermally responsive polymer gel composition of the present invention, the tube having a first end and a second end, and an internal lumen therebetween, said tube being maintained at a temperature lower than a shrinking temperature of the polymer gel composition; (b) providing a blood vessel system comprising a first blood vessel segment having an internal lumen and an end and a second blood vessel segment having an internal lumen and an end, said system being within a warm-blooded animal having a minimal internal ambient temperature that is greater than the shrinking temperature of the polymer gel composition; (c) inserting the end of the first blood vessel segment into the first end of the tube and all the way through the tube such that the end of the first blood vessel segment emerges from the second end of the tube; (d) connecting the end of the first blood vessel segment with the end of the second blood vessel segment with at least one surgical stitch; (e) positioning the tube over the first end and second end of the first and second blood vessel segments, respectively; and (f) maintaining the tube in position until the temperature of the tube achieves the internal ambient temperature of the animal and shrinks onto the blood vessel segments, thereby providing contiguous blood flow through the two blood vessel segments and sealing the blood vessel system.

Such a method may also be used ex vivo. In this instance, the blood vessel segments are maintained outside the animal body at a temperature lower than the shrinking temperature. Following positioning of the tube around the segments, the temperature of the tube is warmed to a temperature equal to or greater than the internal ambient temperature of the animal into which the segments and tube are to be reinserted, thus permitting the tube to shrink around the segments and to hold them tightly. The segments and tube may then be reinserted into the animal body.

In such methods, the polymer gel composition may comprise, for example, a hydrophobic polymer matrix and an interpenetrating hydrophilic polymer network disposed within said hydrophobic polymer matrix, wherein said polymer gel composition has an enhanced thermal responsiveness as compared to the hydrophobic polymer matrix alone. PNIPAAM is a preferred hydrophobic polymer matrix and gelatin is a preferred interpenetrating hydrophilic polymer network for use in such methods.

In one embodiment of such methods for sealing a blood vessel system, the tube may maintained at a temperature of no more than about 32° C., and the warm-blooded animal may have a minimal internal ambient temperature of from about 25° C. to about 40° C., and more preferably, at least about 35° C.

Also provided by this invention are methods for reinforcing a blood vessel segment or a nerve segment in vivo in a warm-blooded animal having a minimal internal ambient temperature of at least about 33° C. Such methods comprise the steps of: providing a sheet comprising a thermally responsive polymer gel composition of the invention, said sheet being maintained at a temperature of no more than about 30° C.; contacting said blood vessel segment or said nerve segment with the sheet, said blood vessel segment or said nerve segment being contained within the animal; using an applicator to form the sheet into a tube around said blood vessel segment or said nerve segment; and maintaining the tube in position until the temperature of the tube achieves the internal ambient temperature of the animal and contacts said blood vessel segment or said nerve segment, thereby reinforcing the blood vessel segment or nerve segment.

Figure 4A:
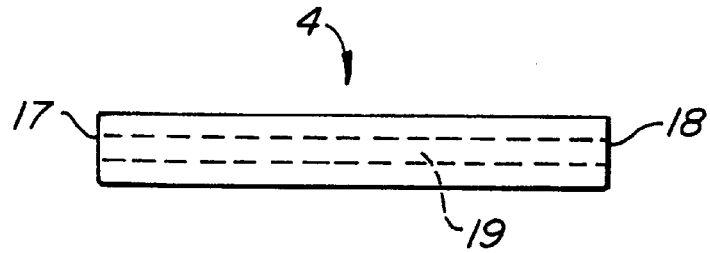
FIG. 4A is a schematic illustration of a tube comprising a thermally responsive polymer gel of the present invention at 20° C. that is suitable for use in methods and applications according to the present invention.
Figure 4B:
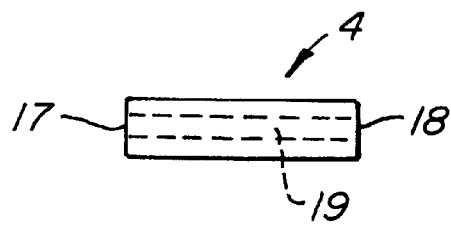
FIG. 4B is a schematic illustration of a tube comprising a thermally responsive polymer gel of the present invention at 37° C. that is suitable for use in methods and applications according to the present invention.

FIG. 4A illustrates another aspect of the present invention. FIG. 4A shows a tube (4) comprising a thermally responsive polymer gel composition of the invention which comprises a hydrophobic polymer matrix and an interpenetrating hydrophilic polymer network disposed within the hydrophobic polymer matrix at a temperature of about 20° C. The tube (4) has a first end (17) and a second end (18), and an internal lumen (19) therebetween. FIG. 4B shows the same tube (4) at a temperature of about 37° C.

In one embodiment, the hydrophobic polymer matrix comprises PNIPAAM and the interpenetrating hydrophilic polymer network comprises a protein, such as collagen or gelatin. In a preferred embodiment, the interpenetrating hydrophilic polymer network of the polymer gel composition comprises at least 1% gelatin by weight based on the total weight of the composition. As illustrated in FIGS. 4A and 4B, when the tube (4) is heated from 20° C. to 37° C., the tube shrinks.

Figure 4C:
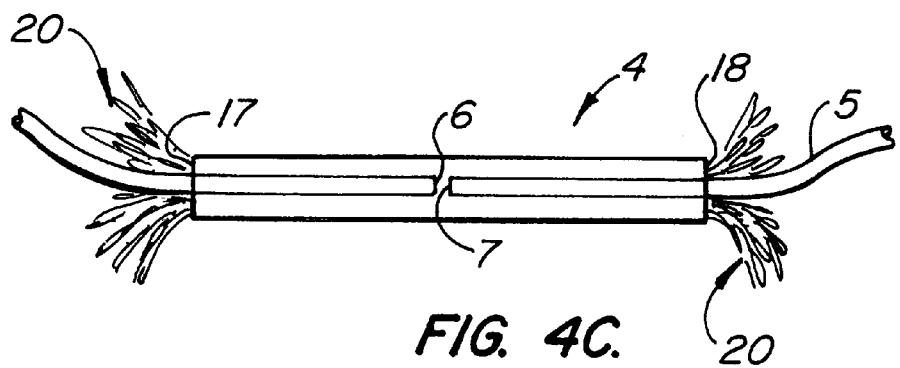
FIG. 4C is a schematic illustration of a tube comprising a composition of the invention maintained at a temperature of about 20° C. and into which two ends of a severed blood vessel have been inserted.

FIG. 4C, which presents another embodiment of the present invention, is a schematic illustration of an in vitro (or in vivo) use of a tube (4), said tube having a first end (17) and a second end (18). The tube comprises a polymer gel composition of the present invention to seal or connect a severed or ruptured blood vessel (5). In this embodiment, the non-shrunken polymer gel tube (4) is positioned around the rupture point of the blood vessel such that the two severed ends of the blood vessel are encompassed by the tube. The first end (6) and second end (7) of the severed blood vessel (5) are inserted into the lumen of the tube (4) while the tube (4) is maintained at a temperature lower than the shrinking temperature of the polymer gel composition of which it is made (e.g., about 20° C.). The first end (6) and the second end (7) of the blood vessel are brought together and tube (4) is placed over these ends. The tube (4) loosely holds the first and second ends of the blood vessel together, and blood (20) is observed to flow from the ends of the vessel out through the first end (17) and second end (18) of the tube.

Figure 4D:
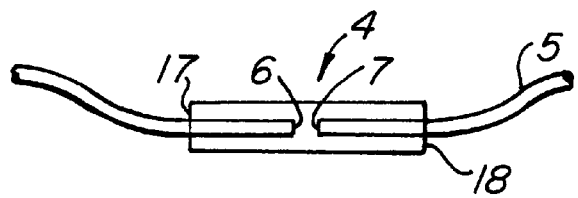
FIG. 4D is a schematic illustration of the tube depicted in FIG. 4C after heating the tube depicted in FIG. 4C to about 37° C.

FIG. 4D depicts the blood vessel (5) and tube (4) after heating to a temperature equal to or greater than the shrinking temperature of the polymer gel composition (e.g., for PNIPAAM/gelatin, the shrinking temperature is about 37° C.). In response to the increase in temperature, the tube (4) shrinks, thereby contacting and gripping the first end (5) and second end (6) of the blood vessel (5) tightly, thereby permitting blood to flow from the first and second end of the blood vessel (i.e., through the blood vessel), but preventing blood from flowing out of the first end (17) and second end (18) of the tube (4). Thus, the severed blood vessel (5) is effectively sealed and repaired, and leakage of blood into the environment surrounding the vessel is prevented.

In general, a tube comprising a polymer gel composition of the present invention seals a severed blood vessel and prevents further leakage of blood from the vessel into the surrounding environment for a blood flow rate of more than 1 milliliter per second (mL/sec) or a flow speed of more than 5 meters per second (m/sec).

In another aspect, the invention provides methods for joining a first nerve segment and a second nerve segment of a nerve system in vivo or ex vivo in a warm-blooded animal comprising the steps of: (a) providing a tube comprising a thermally responsive polymer gel composition of the invention, the tube having a first end and a second end, and an internal lumen therebetween, and the tube being maintained at a temperature lower than a shrinking temperature of the polymer gel composition; (b) providing a nerve system comprising a first nerve segment having an end and a second nerve segment having an end, said first and second nerve segments being within a warm-blooded animal having a minimal internal ambient temperature that is greater than the shrinking temperature of the polymer gel composition; (c) inserting the end of the first nerve segment into the first end of the tube and through the tube such that the end of the first nerve segment emerges from the second end of the tube; (d) connecting the end of the first nerve segment with the end of the second nerve segment with at least one surgical stitch; (e) positioning the tube over the ends of the first and second nerve segments; and (f) maintaining the tube in position until the temperature of the tube equilibrates with the internal ambient temperature of the animal and shrinks onto the nerve segments, thereby joining the first and second nerve segments.

The polymer gel compositions of the invention may also be used in forming temperature-dependent implantable medical devices and drug delivery for use in a variety of applications, including surgical application described herein. Such devices and systems are useful, for example, in the delivery of drugs or other biologically or physiologically active compounds in the body of subjects in need of such treatment, including humans and animals, and in joining separated tissues or repairing damaged tissues (e.g., blood vessels or nerves) or reinforcing or augmenting structurally deficient tissues, vessels or nerves.

The implantable medical devices and systems of the invention may be formed of various shapes and sizes, including sheets and tubes. Such devices, particularly when formed in sheets or tubes, are especially useful in various medical and surgical applications, including in vivo and ex vivo repair of damaged, ruptured, or severed blood vessels and neurons, repair of damaged or separated tissues, and reinforcement of weakened or structurally deficient tissues, vessels, and neurons.

When implantable medical devices comprising polymer gel compositions of the invention are used as drug delivery systems or as components of such systems, they typically include one or more drugs, biologically or physiologically active compounds, or the like. The compound is capable of being released from the gel composition when the gel composition shrinks in response to an increase in temperature. The gel composition of the present invention which includes a hydrophilic IPN network releases the compound much more quickly at a particular site in the body of the subject in response to the change of temperature than does a gel composition that does not include a hydrophilic IPN network.

Each such biologically or physiologically active compound may be incorporated into the matrix network of the polymer gel composition by using various procedures that are well known in the art. For example, a drug or other biologically or physiologically active compound may be incorporated into a polymer gel composition of a temperature-dependent implantable medical device by a standard "loading" process. A variety of methods well-known in the art can be employed to incorporate or "load" such drugs or other biologically or physiologically active compounds into the polymer gel composition, including those methods described below. See, e.g., Y. H. Kim et al., *J. Controlled Release* 28:143 (1994), R. Yoshida et al., *J. Biomat. Sci.-Polym. Ed.* 6:585 (1994), and A. S. Hoffman, *J. Controlled Release* 6:297 (1987), which are incorporated herein in their entirety for all purposes.

In one aspect, the invention provides methods for releasing the biologically or physiologically active compound comprising the steps of: (a) providing an implantable medical device, said device comprising the thermally responsive polymer gel composition of the present invention and a therapeutically effective amount of the biologically or physiologically active compound, said device being maintained at a temperature less than a shrinking temperature of the composition, said compound being released from the composition when a temperature of the composition is increased to a temperature equal to or greater than the shrinking temperature of the composition; (b) implanting said device in a body of a warm-blooded animal having a minimal internal ambient temperature greater than the shrinking temperature of the composition; and (c) allowing the temperature of the device to achieve the minimal internal ambient temperature of the animal such that the composition shrinks and the compound is released from the composition. A therapeutically effective amount is an amount adequate to effect a therapeutic result in more than 50% of subjects, including animals and humans so treated. The therapeutically effective amount will depend, among other things, on the body weight, physiology, and chosen method of administration.

The invention also provides methods for site-specific or systemic drug delivery which comprise implanting into the body of a subject in need thereof, including a warm-animal or a human having a minimal internal ambient temperature (e.g., from about 25° C. to about 40° C., and more preferably, at least about 35° C.), a temperature-dependent implantable medical device comprising a thermally responsive polymer gel composition of the invention (including a biocompatible polymer gel composition) and a therapeutically effective amount of a biologically or physiologically active compound. The animal has a minimal internal ambient temperature that is greater than the shrinking temperature of the composition. The compound is capable of being released from the gel composition and delivered into the animal when the gel composition shrinks in response to an increase in temperature. Prior to implantation, the device is maintained at a temperature of about 2° C. to about 3° C. lower than the shrinking temperature of the gel compositions (e.g., typically no more than about 32° C.). At the normal internal ambient temperature, the device will not release the compound, but when the temperature around the implanted gel rises about 2° C. to about 3° C. above the normal ambient temperature, the compound is released.

Such methods comprise implanting the device comprising polymer gel of the invention in the body of the animal and allowing the temperature of the gel composition of the device to increase and equilibrate with the body temperature of the animal. As the temperature of the gel composition increases and (rises above the critical solution temperature), the gel composition shrinks and releases the compound from the gel composition, thereby delivering the compound into the animal.

Drug delivery systems comprising polymer gel compositions of the invention may be prepared and employed as described herein and may be prepared and used by and in procedures well-known to those of ordinary skill in the art, including, e.g., the methods and applications described in: K. P. Rao, *J. Biomater. Sci. Poly. Edn.,* 7(7):623–645 (1995); M. Mahoney et al., *J. Pharm. Sci.,* 85(12) :1276–1281 (1996); and L. Brannon-Peppas, *Int'l J. Pharmaceutics* 116, 1–9 1995).

In another aspect, the invention provides methods of releasing a chemical into an environment by using a thermally responsive polymer gel composition of the invention, such as PNIPAAM/gelatin polymer gel composition, into which a chemical is incorporated. The chemical is capable of being released from the gel composition when the gel composition shrinks in response to an increase in temperature. Such methods comprise providing a gel composition of the invention and increasing the temperature of the gel composition such that the gel composition shrinks and thereby releases the chemical from the gel composition.

A variety of well-known methods can be utilized to load or incorporate a desired chemical into the gel composition. In one method, for example, such a chemical is placed into the pre-gel solution containing the monomers and hydrophilic polymers. Polymerization of the monomers leads to a thermally sensitive gel network which includes the chemicals and the hydrophilic polymers. The hydrophilic polymers can be further cross-linked to form an IPN.

The monomers react with each other to form the thermally sensitive gel network which is hydrophobic at higher temperatures. For example, in the PNIPAAM gel, NIPAAM (n-isopropylacrylamide) is the monomer. The solution typically contains (by weight) about 10% monomers, about 0.5 to about 5% hydrophilic polymers, and some crosslinking agent and other chemicals. During the polymerization process, all of the monomers and crosslinking agents interconnect with each other to form a three-dimensional network in which the hydrophilic polymers are trapped. Such a network is termed a "semi-interpenetrating polymer network." The hydrophilic polymers trapped inside the thermally sensitive gel network can be further cross-linked to form an interpenetrating gel network which contains two sets of polymer networks.

Additionally, the polymer gel compositions of the invention are useful in a wide variety of applications where thermally sensitive materials are desired, such as, for example, for use as temperature-sensitive membranes or barriers. The preferred polymer gel compositions for use as temperature-sensitive membranes include gelatin in an amount of from about 0.1% to about 25% by weight, and preferably from about 0.5% to about 5% by weight, and PNIPAAM in an amount of from about 5% to about 30% by weight, based on the total weight of the gel composition.

The polymer gel compositions may be useful in a bilayer format to provide a thermally responsive actuator. In one embodiment, an actuator comprises a polymer gel layer comprising a thermally responsive polymer gel composition disposed over a flexible planar element, such as a thin poly(styrene) film, that is not affected or at least not substantially affected by a change in temperature (i.e., thermally non-responsive or at least substantially thermally non-responsive). By "substantially thermally non-responsive" is meant that a flexible planar element, for example does not shrink substantially in response to an increase in temperature. In this embodiment, the thermally responsive polymer gel composition comprises a hydrophobic polymer matrix and an interpenetrating polymer network disposed within the hydrophobic polymer matrix, wherein the polymer composition has enhanced thermal responsiveness as compared to the hydrophobic polymer matrix alone.

In another embodiment, an actuator can be made in a bilayer format as follows. A gel composition according to the present invention is prepared, formed into a strip or sheet (or other suitable shape or configuration), and stored in an aqueous solvent, such as water, such that it is in its swollen state. A portion of the strip (e.g., one-half of the strip) is modified by cross-linking using a monomer that is not present in the strip so as to form a network that is not thermally responsive to heat or to a change in temperature. Such cross-linking may be accomplished, for example, by immersing a portion of the strip in a solution containing such a monomer. The resulting strip or sheet will comprise a bilayer, with one layer having thermally responsive properties and the second layer having no or little thermally responsive properties. The thickness and size of the strip or sheet for use an actuator will depend on the particular application (e.g., 1 mm to 1 cm). Alternatively, the actuator may comprise a bilayer format in which the first layer includes a hydrophilic IPN, while the second layer includes a hydrophobic IPN.

In another aspect, the invention provides drug carriers comprising the polymer gel compositions of the invention. Such carriers are useful in delivering drugs to subjects in need of such treatment. The drug carrier is designed to match the particular delivery application needed for the drug (e.g., oral delivery, delivery by implantation of device or material comprising polymer gel composition). For example, if the drug is to be delivered orally, the carrier and polymer gel composition are designed and selected specifically for successful oral delivery, with attention being given to protecting against poor absorption across the gastrointestinal mucosa, protection against enzymatic degradation, and protection from the acidic environment of the stomach. To aid in successful oral delivery, additional components, such as enzyme inhibitors, permeation enhancers, and drug stabilizers, may be incorporated into the carrier comprising at least one polymer gel composition of the invention.

In yet another aspect, the invention sets forth methods of producing a thermally responsive polymer gel composition comprising at least one hydrophobic polymer matrix and at least one interpenetrating hydrophilic polymer network disposed within the hydrophilic polymer network. Such methods typically comprise the steps of: (a) combining the hydrophobic polymer matrix and the interpenetrating hydrophilic polymer network; (b) agitating the product obtained from step (a) to form a mixture; and (c) placing the product step (b) into a vessel adapted to store or deliver the composition. Methods for producing polymer gel compositions of the invention are also set forth below in the Examples.

The present invention is further illustrated by the following examples. These examples are merely to illustrate aspects of the present invention and are not intended as limitations of this invention.

EXAMPLES

Example 1

Synthesis of PNIPAAM/Protein IPN Gel

NIPAAM/gelatin IPNs containing 0.5 to 5% gelatin were synthesized by the following procedure. N-isopropylacrylamide (NIPAAM) was obtained from Kohjin Co., Ltd., Japan. Pharmaceutical grade B-type gelatin (Bloom value 270, in solid form) was obtained from Deutsche Gelatine-Fabriken Sloess. A concentrated NIPAAM solution was prepared by dissolving 3.98 g NIPAAM, 0.068 g N,N'-methylenebis(acrylamide), and 0.122 mL of N,N,N',N'-Tetramethylthylene diamine in sufficient deionized water to achieve a total volume of 25 mL. An aqueous solution of 5.16% gelatin (w/w) in deionized water was prepared by dissolving the appropriate amount of gelatin in deionized water. A potassium persulfate (KPS) solution was prepared by dissolving 0.12 g potassium persulfate in 5 mL deionized water. The solutions were stored at about 4 to 6° C. until used.

Polymerization of NIPAAM: The gelation solution was heated to about 55° C. while stirring until the gelatin melted completely. After the gelatin solution cooled to about 30 to about 35° C., 1.53 mL of the gelatin solution was mixed with 1.47 mL deionized water, and then 3.0 mL NIPAAM solution was added. The mixture was stirred for several minutes, and then 0.12 mL KPS was added to the mixture. The mixture was then immediately injected into a mold having the shape of the desired device (e.g., flat sheet or tube). The mold was placed in a sealed vessel. Oxygen was removed repeatedly by degassing the mixture using nitrogen at least three times. The mixture was allowed to polymerize for at least two hours at room temperature.

Cross-linking of gelatin: After complete polymerization, the gel was removed from the mold and immersed into an aqueous solution of 0.5% gluctaric dialdehyde to cause the gelatin chains inside the PNIPAAM gel to become cross-linked, thereby forming an interpenetrating network. The resultant gel device was washed with deionized water over the course of several days (by changing the water each day) to remove remaining small molecules and unreacted NIPAAM monomers. The clean gel device was stored at 4–6° C. The thickness of a gel sheet or gel tube formed by this procedure typically ranges from about 0.2 to about 3 mm.

The above procedure can be modified, as necessary, to prepare a hydrophobic polymer matrix having incorporated therein an interpenetrating polymer network of a different protein(s).

In the case of loading a drug into a gel composition (e.g., in preparing a drug delivery system or device), the chemicals to be loaded into the gel can be added to the NIPAAM solution or gelatin solution before the polymerization process, or, alternatively, can be added to the aqueous gluctaric dialdehyde solution before the gelatin cross-linking process. Such drug delivery systems or devices (including implantable medical devices) comprising thermally responsive polymer gel compositions of the invention are useful in a variety of applications, including those identified and described herein. A variety of drugs may be included in such drug delivery systems and devices. The particular drug to be incorporated in such systems and devices will depend upon the particular application and the nature of the disease or condition to be treated.

Example 2

Animal Experiments of Poly(N-isopropylacrylamide)/gelatin gel

After the modification of PNIPAAM gel by inducing a hydrophilic gelatin network, the shrinking rate at about 37° C. increases about $10^3$ times. Given these properties, this thermally responsive polymer gel composition can be used in surgery to facilitate tissue recovery and simplify the operation. A series of primary in vivo experiments were conducted on rats to investigate tissue reactions to this PNIPAAM/gelatin gel composition and uses of this composition in repairing tendon and sciatic nerves by direct application in surgical procedures.

1. Tissue Reactions

Figure 5:
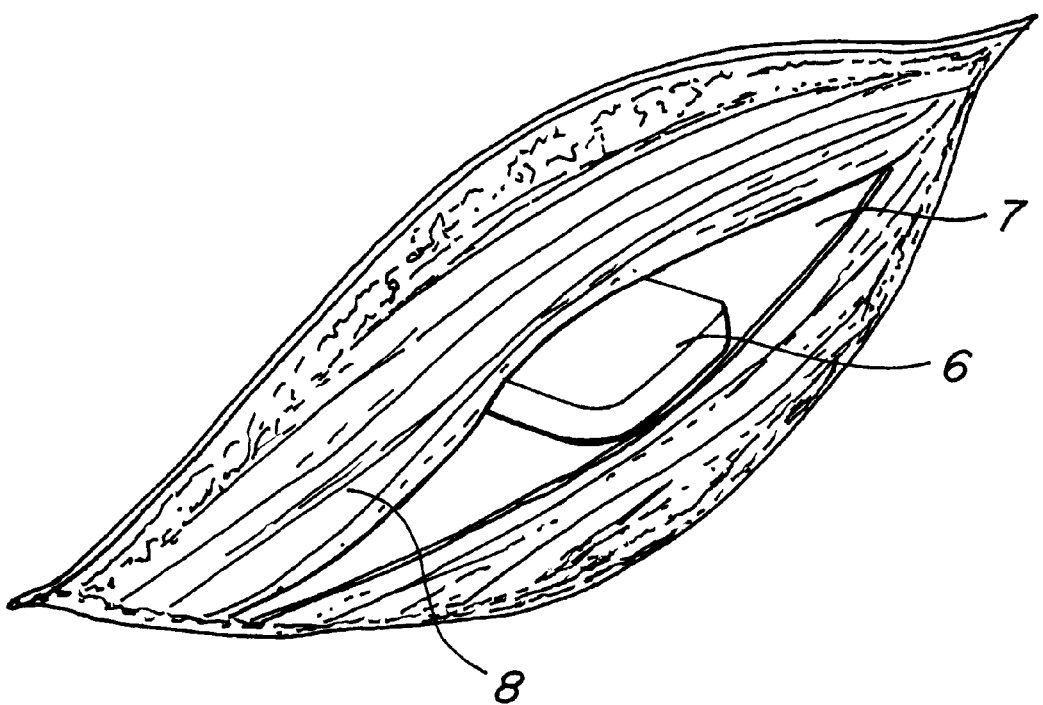
FIG. 5 is a schematic illustration showing the implantation of thermally responsive polymer gel piece constructed according to principles of the invention inserted between the peritoneum and rectus abdominis of an animal.

Mature rats with a weight of 400–500 g were used for in vivo experiments. To test reaction of various tissues to the PNIPAAM/gelatin (ratio of relative amount of PNIPAAM/gelatin is 1.0/0.16 (w/w)) polymer gel composition, flat square pieces (approximately $8\times8\times1$ mm$^3$) of the PNIPAAM/gelatin polymer gel composition swollen in deionized water in equilibrium swelling state were implanted, respectively, inside different parts of the animal body as follows: (a) between the rectus abdominis and peritoneum (FIG. 5); (b) among the femoral artery, femoral nerve, and femoral vein of the groin (FIG. 6); and (c) subdermally in the gluteus maximus (FIG. 7). The peritoneum is the serous sac consisting of mesothelium and a thin layer of irregular connective tissue that lines the abdominal cavity and covers most of the viscera contained therein. STEDMAN'S MEDICAL DICTIONARY (26th ed. 1995).

FIG. 5 shows a schematic illustration of the implantation of a flat square piece ($8\times8\times1$ mm$^3$) of PNIPAAM/gelatin polymer gel composition (6) prepared according to the present invention. The gel piece (6) is inserted into between the peritoneum (7) and rectus abdominis (8) within the animal. The ratio of the relative amount of gelatin to PNIPAAM in the gel piece is 0.16 to 1.0.

Figure 6:
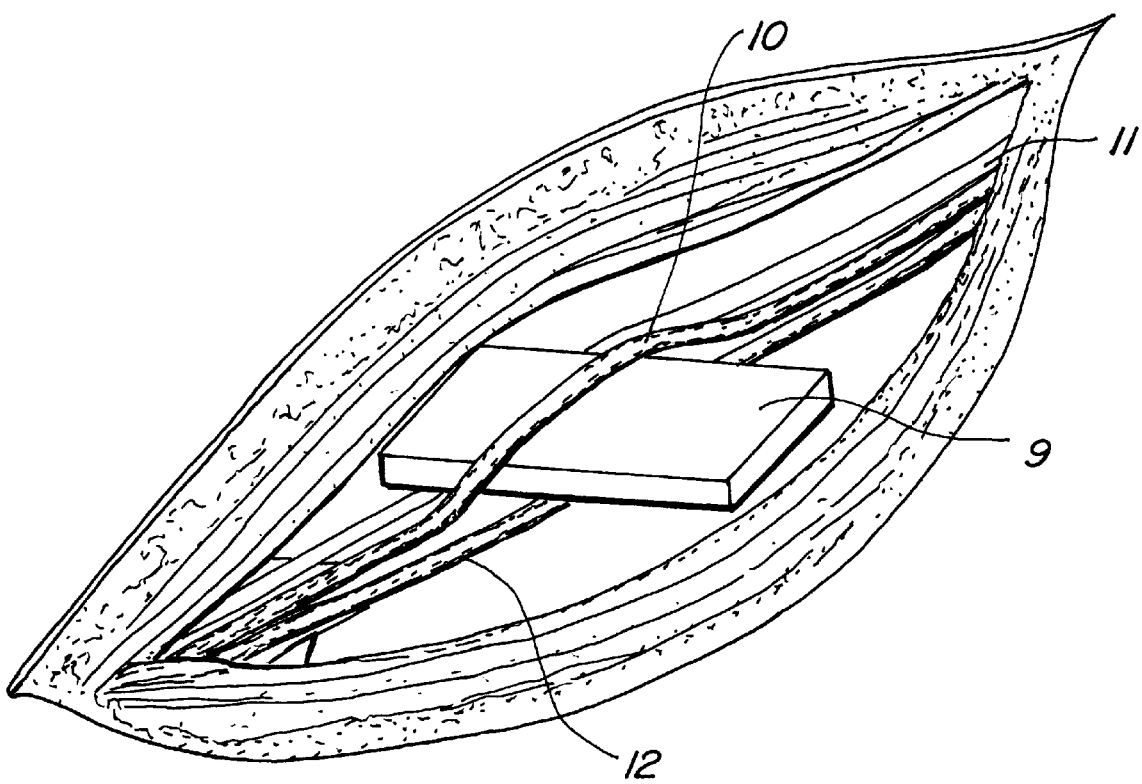
FIG. 6 is a schematic illustration depicting the implantation of a thermally responsive polymer gel piece constructed according to principles of the invention inserted between the femoral artery, femoral nerve, and femoral veins of the groin of an animal.
Figure 7:
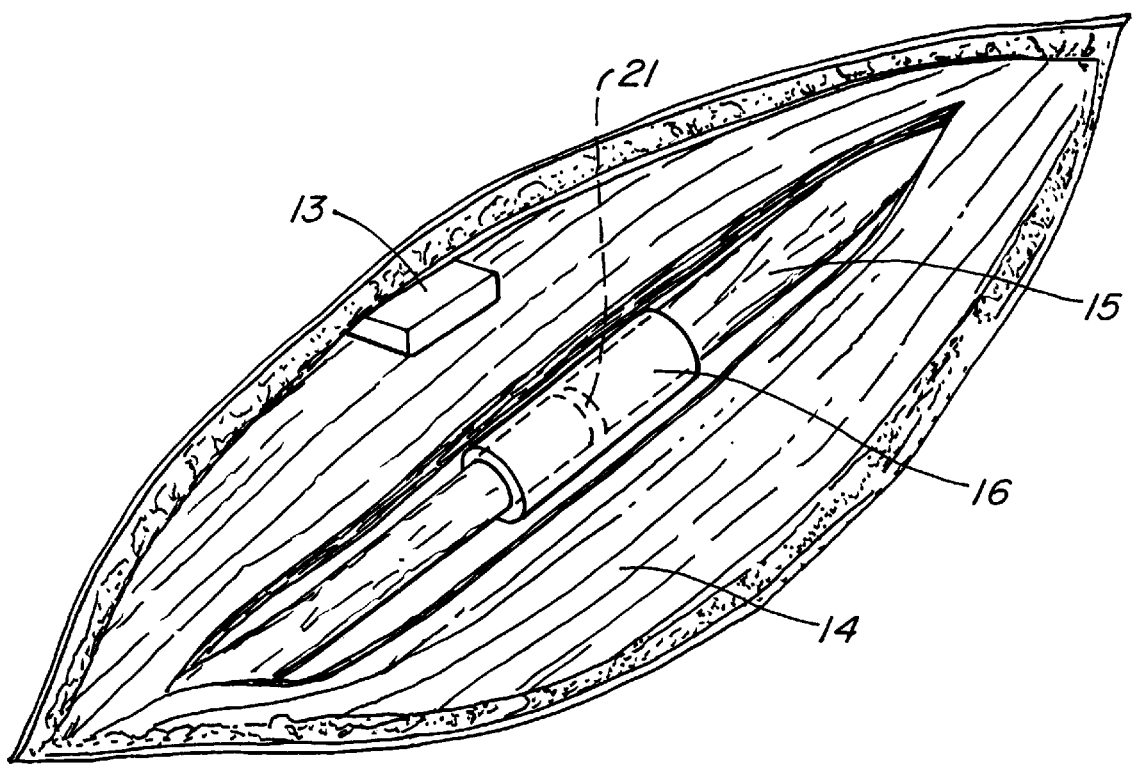
FIG. 7 shows a schematic illustration showing the subdermal implantation in the gluteus maximus muscle of an animal of a thermally responsive polymer gel piece constructed according to principles of the invention and suitable uses of such a gel piece to connect and/or repair a severed sciatic nerve of the animal.

FIG. 6 shows a schematic illustration of the implantation of a flat square piece ($8\times8\times1$ mm$^3$) of PNIPAAM/gelatin polymer gel composition (9) preparing according to the present invention implanted into the groin of the animal. This gel piece (9) is inserted between the femoral artery (10), femoral nerve (11), and femoral vein (12) of the groin. The ratio of the relative amount of gelatin to PNIPAAM in this composition is 0.16 to 1.00.

FIG. 7 shows a schematic illustration of a subdermal implantation in the gluteus maximus muscle (14) of the animal of a flat square piece ($8\times8\times1$ mm$^3$) of PNIPAAM/gelatin polymer gel composition (13) prepared according to the present invention and inserted subdermally in the gluteus maximus (14) of the animal. The ratio of the relative amount of gelatin to PNIPAAM in this gel piece is 0.16 to 1.00.

FIG. 7 also presents a schematic illustration of a subdermal implantation in the gluteus maximus muscle (14) of the animal of a tube (16) comprising a PNIPAAM/gelatin polymer gel composition prepared according to the present invention that is positioned around and encases a ruptured or severed point (21) of a sciatic nerve (15).

Each operation site was opened and checked after 3 days, 1 week, and 2 weeks, respectively, to observe the tissue reactions and to obtain histological examinations. No effusion or infection was observed around the gel pieces. The hyperemia and adhesion properties were consistent with those observed in a normal surgical operation. In addition, the circulation was not involved. The gel piece placed in the abdomen, as shown schematically in FIG. 5, had an initial area of about 8×8 mm² when fully swollen in deionized water, but contracted to an area of about 4×4 mm² and became translucent inside the abdomen after about ten minutes.

The gel piece implanted in the groin (6) and the gel pieces implanted subdermally in the gluteus maximus ((13) and (16)) disappeared after three days. This can be attributed to the lower body temperature (approximately 32° C.) in the groin and subdermally in the gluteus maximus. At such temperature, the gel is in its swollen state and has a much lower strength. As a result, the gel pieces implanted in the groin and implanted subdermally were crushed to small pieces and merged with the surrounding tissue during the process of wound recovery. This effect is easily overcome by adjusting the shrinking temperature of the gel composition to a lower value by varying the relative amounts of the hydrophobic polymer (e.g., PNIPAAM) and interpenetrating hydrophilic polymer network disposed therein (e.g., gelatin), as described above.

The results of this experiment demonstrate that the PNIPAAM/gelatin gel composition induces no significant tissue reaction on muscle, blood vessel, or nerve tissue. The tissue reactions are summarized in Table 1 below.

TABLE 1

Summary of Tissue Reactions

| Implantation sites* | Effusion/ Infection 3 days / 1 week / 2 weeks | Hyperemia/ Adhesion 3 days / 1 week / 2 weeks | Circulation 3 days / 1 week / 2 weeks | Gel state |
|---|---|---|---|---|
| abdomen | no / no / no | normal/normal/ normal | NI**/NI/NI | contracted and translucent |
| groin | no / no / no | normal/normal/ normal | NI/NI/NI | cracked |
| subdermal | no / no / no | normal/normal/ normal | NI/NI/NI | cracked |

*:Refer to FIGS. 1–3.
**:"NI" denotes "not involved"

2. Repair of Sciatic Nerve

The use of a tube comprising a PNIPAAM/gelatin polymer gel composition of the present invention in repairing a sciatic nerve of a warm-blooded animal using was studied as follows. PNIPAAM/gelatin (1.0/0.16 (w/w)) tubes having an inside diameter of 2.1 mm, a thickness of 1 mm, and a length of about 6 mm were prepared and stored in deionized water. The diameter of sciatic nerve of a mature rat ranges from about 1.5 to about 2.0 mm.

The operation procedure was conducted as follows: After cutting the sciatic nerve, one end of the nerve was threaded through the PNIPAAM/gelatin tube. Both ends of the nerve were then connected using one or two stitches. (At least 8 are typically required to connect two severed nerve ends if no tube is used; thus, the use of the tube (or similar device) according to the present invention reduces the number of stitches normally required to connect a severed nerve or the like (e.g., blood vessel). After this connection was made, the tube was moved to cover the connected nerve ends. Around the sciatic nerve, the temperature is typically higher than the gel shrinking temperature (e.g., about 35° C.) at which this particular PNIPAAM/gelatin composition reaches its fully collapsed state, so that the shrinking gel tube collapsed about the two ends of the nerve, holding such ends tightly and pulling them together.

The nerve was checked after 3 days, 1 week, 2 weeks, and 3 weeks to observe the process of recovery. No effusion or infection was observed on the nerve or the surrounding tissue. The nerve was swollen by a factor of approximately 2 at 2 weeks following the operation. After 3 weeks, this swelling was observed to decrease and fine blood cells were observed on the surface of the nerve.

The gel tube has two principal functions: (1) it serves to hold the two ends of the nerve tightly so that the number of the stitches required to hold the severed ends of the nerve in place and to connect them is decreased; alternatively, when the gel tube is employed, no stitches may be needed to hold the severed ends of the nerve in place and to connect them. Thus, with the use of the gel tube, the operation can be performed much more easily and quickly. In addition, the use of the tube in surgical procedures decreases the stitch-induced scar which may decrease the transmittance of the nerve. (2) The gel tube prevents against growth of adjacent or surrounding tissue or other tissue between the severed ends of the nerve, which also decreases the transmittance of nerve.

Although described in terms of specific polymer gel compositions, it will be readily apparent from the instant disclosure that the invention can also be used to make other types of fast-shrinking and stronger polymer gels provided the introduced interpenetrating polymer network is hydrophilic at a temperature higher than the shrinking temperature of the original polymer gel. Such polymer gels can be used in a variety of applications, including those discussed above.

While the foregoing invention has been described in some detail for purposes of clarity and understanding, it will be clear to one skilled in the art from a reading of this disclosure that various changes in form and detail can be made without departing from the true scope of the invention. The above examples are provided to illustrate the invention, but not to limit its scope; other variants of the invention will be readily apparent to those of ordinary skill in the and are encompassed by the claims of the invention. The scope of the invention should, therefore, be determined not with reference to the above description, but instead should be determined with reference to the appended claims along with their full scope of equivalents. All publications, references, and patent documents cited in this application are incorporated by reference in their entirety for all purposes to the same extent as if each individual publication or patent document were so individually denoted.

What is claimed is:

1. A thermally responsive polymer gel composition, comprising:
   a thermosensitive polymer matrix comprising poly(n-isopropylacrylamide) (PNIPAAM) or a derivative thereof; and
   an interpenetrating hydrophilic polymer network disposed within said thermosensitive polymer matrix, said hydrophilic polymer network comprising a protein,
   wherein a shrinking rate of said polymer gel composition is increased by a factor of up to 1000 as compared to the thermosensitive polymer matrix alone at a temperature equal to or greater than a shrinking temperature of the polymer gel composition.

2. The thermally responsive polymer gel composition of claim 1, wherein a shrinking rate of the polymer gel composition is increased or decreased by varying a ratio of an amount of thermosensitive polymer matrix to an amount of interpenetrating hydrophilic polymer network in said polymer gel composition.

3. The thermally responsive polymer gel composition of claim 1, wherein said polymer gel composition further comprises an amount of a hydrophobic monomer or an amount of a hydrophilic monomer sufficient to cause a shrinking temperature of said polymer gel composition to increase or decrease.

4. The thermally responsive polymer gel composition of claim 3, wherein the hydrophobic monomer or hydrophilic monomer copolymerizes with the thermosensitive polymer matrix of said composition.

5. The thermally responsive polymer gel composition of claim 1, wherein the protein is selected from the group consisting of collagen and gelatin.

6. The thermally responsive polymer gel composition of claim 5, wherein the protein is gelatin.

7. The thermally responsive polymer gel composition of claim 6, wherein the shrinking temperature of the polymer gel composition is about 35° C.

8. The thermally responsive polymer gel composition of claim 6, wherein gelatin is selected from the group consisting of gelatin extracted from an acidic medium and gelatin extracted from a basic medium.

9. The thermally responsive polymer gel composition of claim 6, wherein the composition comprises gelatin in an amount of from about 0.1% to about 25% by weight based on the total weight of the composition.

10. The thermally responsive polymer gel composition of claim 9, wherein the composition comprises gelatin in an amount of from about 0.5% to about 5% by weight based on the total weight of the composition.

11. The thermally responsive polymer gel composition of claim 10, wherein the composition comprises gelatin in an amount of from about 1% to about 3% by weight based on the total weight of the composition.

12. The thermally responsive polymer gel composition of claim 1, wherein the enhanced thermal responsiveness comprises an increased gel breaking strength at a temperature lower than a shrinking temperature of the polymer gel composition.

13. A sheet comprising the thermally responsive polymer gel composition of claim 1.

14. A tube comprising the thermally responsive polymer gel composition of claim 1.

15. A composition of matter which comprises a polymer gel comprising a thermally sensitive polymer matrix which comprises poly(n-isopropylacrylamide) (PNIPAAM) or a derivative thereof and a hydrophilic polymer network interpenetrating said thermally sensitive polymer matrix, said hydrophilic polymer network comprising a protein, wherein a shrinking rate of said polymer gel is increased by a factor of up to 1000 in response to a change in temperature as compared to a shrinking rate of the thermally sensitive polymer matrix alone.

16. A thermally responsive biocompatible polymer gel composition, comprising:

a thermosensitive polymer matrix comprising poly(n-isopropylacrylamide (PNIPAAM) or a derivative thereof, wherein said matrix becomes more hydrophobic as the temperature is increased to a temperature equal to or above the shrinking temperature of the matrix; and an interpenetrating hydrophilic polymer network disposed within said thermosensitive polymer matrix, said hydrophilic polymer network comprising a protein interpenetrating the thermosensitive polymer matrix, wherein said thermally responsive biocompatible polymer gel composition has a shrinking rate that is increased by a factor of up to 1000 over a shrinking rate of the thermosensitive polymer matrix alone.

17. The thermally responsive biocompatible polymer gel composition of claim 16, wherein the protein is gelatin.

18. The thermally responsive polymer gel composition of claim 9, further comprising a chemical incorporated into the gel composition, said chemical capable of being released from the composition in response to an increase in the temperature of the gel composition to a temperature above a shrinking temperature of the composition.

19. An interpenetrating polymer network gel composition comprising:

a thermosensitive polymer network comprising poly(n-isopropylacrylamide (PNIPAAM) or a derivative thereof, and a protein interpenetrating the thermosensitive polymer network, the PNIPAAM and the protein arranged with respect to each other so that at least one type of interaction develops between the PNIPAAM and the protein, the at least one type of interaction being sufficient to cause the composition to shrink at a rate of up to a 1000 times greater than a shrinking rate of the thermosensitive polymer network alone at a temperature above a shrinking temperature of the composition.

20. A temperature-dependent implantable medical device comprising a thermally responsive polymer gel composition of claim 16.

21. The implantable medical device of claim 20, wherein said device is in the form of a sheet for use in joining separated tissues or repairing damaged tissues.

22. The implantable medical device of claim 20 for use in reinforcing or augmenting structurally deficient tissues.

23. The implantable medical device of claim 20, further comprising a biologically or physiologically active compound.

24. A temperature-dependent drug delivery system comprising a thermally responsive polymer gel composition of claim 1, said composition further comprising a biologically or physiologically active compound incorporated therein, wherein said compound is released from the composition in response to an increase in a temperature of the composition.

25. The temperature-dependent drug delivery system of claim 24, wherein the chemical is released from the composition when the temperature of the composition is increased to a temperature equal to or greater than the shrinking temperature of the composition.

26. A method of releasing a chemical into an environment, comprising the steps of:

providing a thermally responsive polymer gel composition of claim 1, wherein said composition further comprises a chemical; and increasing a temperature of the composition to a temperature greater than the shrinking temperature of the composition such that the chemical is released from the composition into the environment.

27. A thermally responsive actuator comprising a thermally responsive polymer gel composition of claim 1 disposed over a flexible planar element, wherein said flexible planar is not substantially thermally responsive.

28. The thermally responsive polymer gel composition of claim 1, wherein poly(n-isopropylacrylamide) (PNIPAAM) is modified by copolymerization with a monomer selected from the group consisting of acrylate, acrylic acid, methacrylate, methacrylic acid, acrylamide, methacrylamide, vinyl acetate, styrene, and derivatives thereof.

\* \* \* \* \*